Nov. 21, 1950 H. F. BOHNE Plant Pat. 990
PHILODENDRON PLANT
Filed Sept. 14, 1949
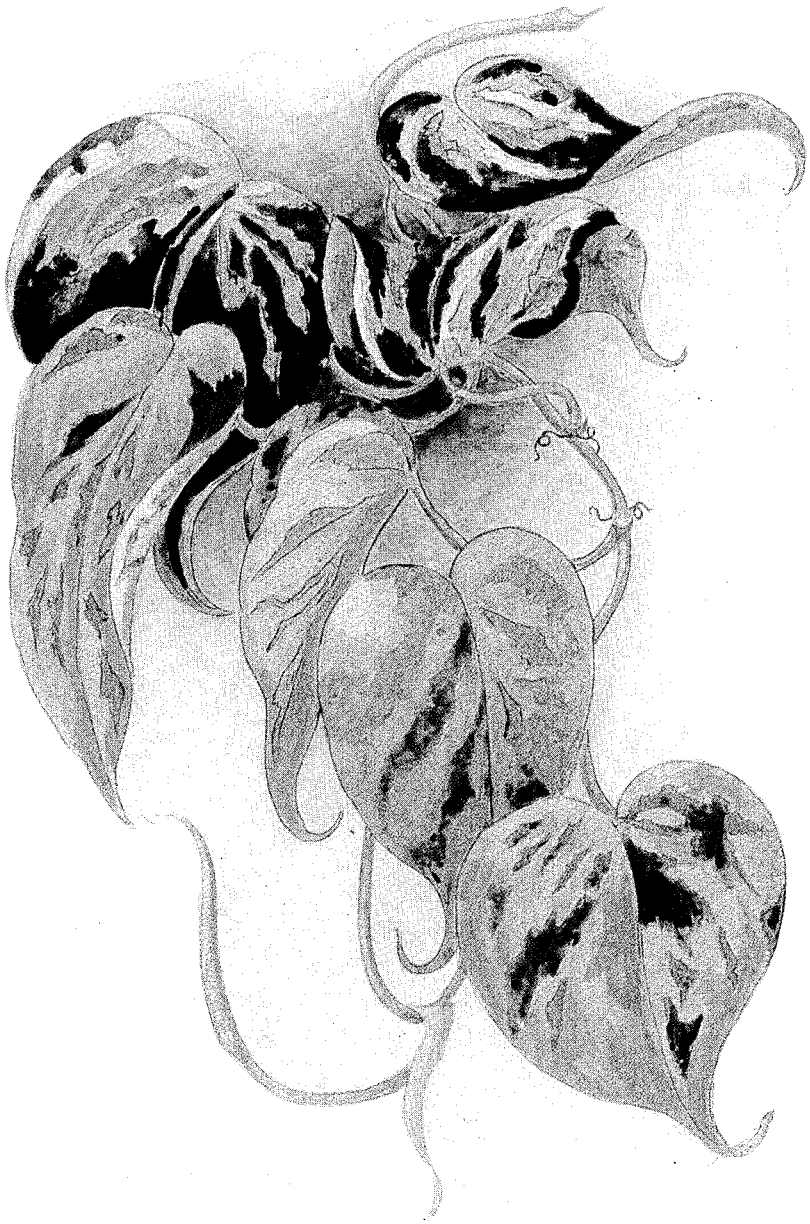
WITNESS
Addison E. Avery
INVENTOR,
HENRY F. BOHNE,
by Rummler Rummler & Snow,
ATTYS.

Patented Nov. 21, 1950

Plant Pat. 990

UNITED STATES PATENT OFFICE

990

PHILODENDRON PLANT

Henry Frank Bohne, Middletown, Ohio

Application September 14, 1949, Serial No. 115,583

1 Claim. (Cl. 47—59)

The present variety of philodendron plant originated as a sport of *Philodendron cordatum* discovered in the course of breeding efforts carried on by me since August 1947. Over twelve hundred plants of this new variety have been propagated, some being in the fifth generation, and novel characteristics have been maintained.

Asexual propagation is by cuttings. My development of the variety has been as an indoor plant of ornamental appearance in small state. The vine is sturdy with short stem-joints, dense foliage and a tendency toward branching. When the stem is upright, branches are at 90° angle to the stem. When the stem is hanging, the petoiles leave the stem at an acute angle and turn upward. The leaf is heart shaped, standing at a 90° angle to the adjacent end of its petiole, and having a long downwardly curled cirrose tip. The leaves are characterized as having a marbelized green color with irregular, nonsymmetrical dark areas of no particular pattern interspersed with transluscent areas that are almost white in comparison. These markings are visible on both sides of the leaves and the contrast increases with the edge of the leaf.

The drawing shows the structural and color characteristics of the new variety as exemplified by the terminal portion of a hanging vine, The colors identified in accordance with the charts of Maerz and Paul are shown in the following table:

| Item | Plate | Letter | No. |
|---|---|---|---|
| Bud at tip of stem, a light Silver Green | 18 | H | 5 |
| New fresh leaves, Yellow Green | 18 | L | 6 |
| Dark marking on new leaves | 19 | L | 7 |
| Medium aged leaves—main area | 20 | C | 30 |
| Medium aged leaves—dark markings | 22 | L | 7 |
| Older leaves show 4 distinct greens, including— | | | |
| light areas | 19 | C | 1 |
| darker areas | 20 | B | 3 |
| darker areas | 22 | A | 6 |
| darkest area | 23 | E | 7 |

Under sides of leaves are similarly mottled to their upper sides but of slightly lighter shades.

The foliage is extremely heavy and the internodes of the stem are short, averaging about one inch in length. The leaves are of broad cordate form with a very pointed cirrose tip and without indentations in their edges; the largest being 4½ inches long and 3 inches wide. The petioles are about 2 inches long. The top and bottom surfaces of the leaves are both smooth. The buds are long and slim and occur singly at the end of the stem, comprising a sheath enclosing a growing new stem, leaf and petiole. The sheath withers and falls away as the leaf and stem develop. Branches and roots spring from the stem nodes when conditions for their formation are favorable.

I claim:

A new and distinct variety of philodendron plant, substantially as described and illustrated, characterized by dense foilage of cordate-cirrose leaves with short petioles and with variegated opaque and translucent patternless green markings.

HENRY FRANK BOHNE.

No references cited.